(12) United States Patent
Izawa (10) Patent No.: US 11,698,356 B2
(45) Date of Patent: Jul. 11, 2023

(54) GAS DETECTION DEVICE AND GAS DETECTION METHOD USING METAL-OXIDE SEMICONDUCTOR GAS SENSOR

(71) Applicant: Figaro Engineering Inc., Minoo (JP)

(72) Inventor: Kuniyuki Izawa, Minoo (JP)

(73) Assignee: FIGARO ENGINEERING INC., Osaka (JP)

( * ) Notice: Subject to any disclaimer, the term of this patent is extended or adjusted under 35 U.S.C. 154(b) by 155 days.

(21) Appl. No.: 17/054,893

(22) PCT Filed: Mar. 1, 2019

(86) PCT No.: PCT/JP2019/007999
§ 371 (c)(1),
(2) Date: Nov. 12, 2020

(87) PCT Pub. No.: WO2019/220741
PCT Pub. Date: Nov. 21, 2019

(65) Prior Publication Data
US 2021/0247341 A1 Aug. 12, 2021

(30) Foreign Application Priority Data
May 17, 2018 (JP) .................. 2018-095139

(51) Int. Cl.
*G01N 27/12* (2006.01)
*G01N 33/00* (2006.01)
*G01N 1/24* (2006.01)

(52) U.S. Cl.
CPC .............. *G01N 27/12* (2013.01); *G01N 1/24* (2013.01); *G01N 33/0009* (2013.01);
(Continued)

(58) Field of Classification Search
CPC .. G01N 1/24; G01N 33/0009; G01N 33/0011; G01N 33/0031; G01N 33/0016
(Continued)

(56) References Cited

U.S. PATENT DOCUMENTS 3,887,908 A * 6/1975 Swigert ................ G08B 17/117
340/634
4,007,456 A * 2/1977 Paige ................... G08B 17/117
340/634
(Continued)

FOREIGN PATENT DOCUMENTS

JP 2741381 B2 4/1998
JP 2911928 B2 6/1999
(Continued)

OTHER PUBLICATIONS

Jordi Palacin et al., Application of an Array of Metal-Oxide Semiconductor Gas Sensors in an Assistant Personal Robot for Early Gas Leak Detection, Sensors, www.mdpi.com/journal/sensors, 2019, 16pg(s) (Year: 2019).*
(Continued)

*Primary Examiner* — Stephanie E Bloss
*Assistant Examiner* — Kevin C Butler
(74) *Attorney, Agent, or Firm* — Keating and Bennett, LLP (57) ABSTRACT

A gas detector comprises a metal oxide semiconductor gas sensor whose resistance decreases in reducing gases and a digital information processing device that treats the output of the gas sensor and compares the output with a comparison value for gas detection. The digital information processing device extracts data representing the resistance of the gas sensor in air from the output of the gas sensor and generates the comparison value such that the larger the resistance of the gas sensor in air is, the larger the ratio between the
(Continued)

resistance of the gas sensor in air and a resistance value corresponding to the comparison value is.

3 Claims, 8 Drawing Sheets

(52) U.S. Cl.
CPC ..... *G01N 33/0011* (2013.01); *G01N 33/0016* (2013.01); *G01N 33/0027* (2013.01); *G01N 33/0031* (2013.01); *G01N 33/0067* (2013.01)

(58) Field of Classification Search
USPC ......................................................... 73/23.2
See application file for complete search history.

(56) References Cited

U.S. PATENT DOCUMENTS

| 4,012,692 | A | * | 3/1977 | Eicker | G01N 27/124 |
| | | | | | 422/98 |
| 4,958,513 | A | | 9/1990 | Yasunaga et al. | |
| 10,823,718 | B2 | * | 11/2020 | Murata | G05D 23/19 |
| 11,035,825 | B2 | * | 6/2021 | Carbonelli | G01N 33/0031 |
| 2007/0202012 | A1 | * | 8/2007 | Steichen | G01N 33/0031 |
| | | | | | 422/98 |
| 2019/0145929 | A1 | * | 5/2019 | Carbonelli | G01N 33/0042 |
| | | | | | 204/424 |
| 2020/0319153 | A1 | * | 10/2020 | Makaram | G01N 33/0008 |
| 2020/0326244 | A1 | * | 10/2020 | Yang | G11C 29/021 |
| 2021/0041386 | A1 | * | 2/2021 | Toyota | G01M 3/188 |
| 2021/0247341 | A1 | * | 8/2021 | Izawa | G01N 27/12 |

FOREIGN PATENT DOCUMENTS

| JP | 6830769 | B2 | * | 2/2021 | | |
| WO | WO-2019220741 | A1 | * | 11/2019 | ............. | G01N 27/12 |
| WO | WO-2020246228 | A1 | * | 12/2020 | ............. | G01N 27/12 |
| WO | WO-2022059907 | A1 | * | 3/2022 | | |

OTHER PUBLICATIONS

Phillip J. D. Peterson, Practical Use of Metal Oxide Semiconductor GasSensors for Measuring Nitrogen Dioxide and Ozone in Urban Environments, www.mdpi.com/journal/sensors, Sensors 2017, 25 pg(s) (Year: 2017).*

Blige Saruhan et al., Review: Influences of Semiconductor Metal Oxide Properties on Gas Sensing Characteristics, Frontiers in Sensors, www.frontiersin.org, Apr. 2021, 24 pg(s) (Year: 2021).*

Maria Vesna Nikolic et al., Semiconductor Gas Sensors: Materials, Technology, Design, and Application, Sensors, www.mdpi.com/journal/sensors, 2020, 30 pg(s) (Year: 2020).*

* cited by examiner

| Rair/Rair 0 | Correction Factor C₁ | ... | Correction Factor Ci |
|---|---|---|---|
| 1/16 | 0.16 | | 0.25 |
| 1/8 | 0.25 | | 0.35 |
| 1/4 | 0.4 | | 0.5 |
| 1/2 | 0.63 | | 0.7 |
| 1 | 1 | ... | 1 |
| 2 | 1.6 | | 1.4 |
| 4 | 2.5 | | 2.0 |
| 8 | 4.0 | | 2.8 |
| 16 | 6.3 | | 4.0 | low conc. ←→ high conc.

GAS DETECTION DEVICE AND GAS DETECTION METHOD USING METAL-OXIDE SEMICONDUCTOR GAS SENSOR

FIELD OF THE INVENTION

The present invention relates to gas detection by means of metal oxide semiconductor gas sensors.

BACK-GROUND ART

Accurate detection of low concentration gases by means of metal oxide semiconductor gas sensors is generally difficult since the resistance of the gas sensors fluctuates due to various factors. Regarding this problem, Patent Document 1 (JP2741381B) discloses to sample and store resistance of metal oxide semiconductor gas sensors when the resistance is substantially constant. Then, gases are detected according to the change from the resistance from the stored resistance. Patent Document 2 (JP2911928B) discloses the resistance of metal oxide semiconductor gas sensors remarkably increases in air when SnO2 films in the gas sensors are rapidly cooled to room temperature from a temperature not less than 450 degree Celsius but the resistance does not increase in gases. This phenomenon enables high sensitivity for gas detection at room temperature.

PRIOR DOCUMENT LIST

Patent Document

Patent Document 1: JP2741381B
Patent Document 2: JP2911928B

SUMMARY OF THE INVENTION

Problem to be Solved by the Invention

Patent Document 1 (JP2741381B) uses stationary values of gas sensor resistance, but the stationary values fluctuate due to miscellaneous factors. Therefore, it is difficult to convert the stationary values adequately to values representing the resistances to be expected in gas by multiplication of some constant or the like. The object of the invention is to enable the accurate detection of low concentration gases.

Means for Solving the Problem

A gas detector according to the invention comprises: a metal oxide semiconductor gas sensor whose resistance decreases in reducing gases; and a digital information processing device that treats the output of the gas sensor and compares the output with a comparison value for gas detection in order to detect gas. According to the invention, the digital information processing device extracts data representing the resistance of the gas sensor in air from the output of the gas sensor, preferably, from the distribution of the output of the gas sensor. The digital processing device generates the comparison value such that the larger the resistance of the gas sensor in air is, the larger the ratio of the resistance of the gas sensor in air and a resistance value corresponding to the comparison value is.

A gas detection method according to the invention uses a metal oxide semiconductor gas sensor whose resistance decreases in reducing gases and a digital information processing device that treats the output of the gas sensor and compares the output with a comparison value for gas detection in order to detect gas. The digital information processing device extracts data representing the resistance of the gas sensor in air from the output of the gas sensor, preferably, from the distribution of the output of the gas sensor. The digital processing device generates the comparison value such that the larger the resistance of the gas sensor in air is, the larger the ratio between the resistance of the gas sensor in air and a resistance value corresponding to the comparison value is.

Figure 6:
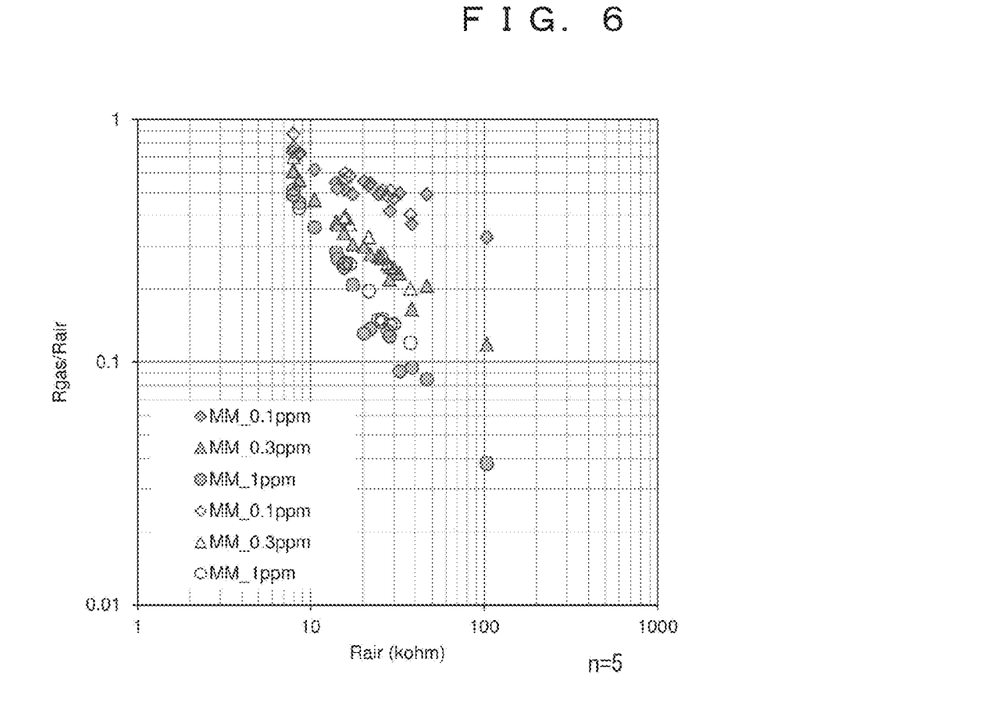
FIG. 6 A characteristic diagram indicating the correlation between the resistance in 0.1 to 1 ppm methyl-mercaptan and the resistance in air (n=5).
Figure 15:
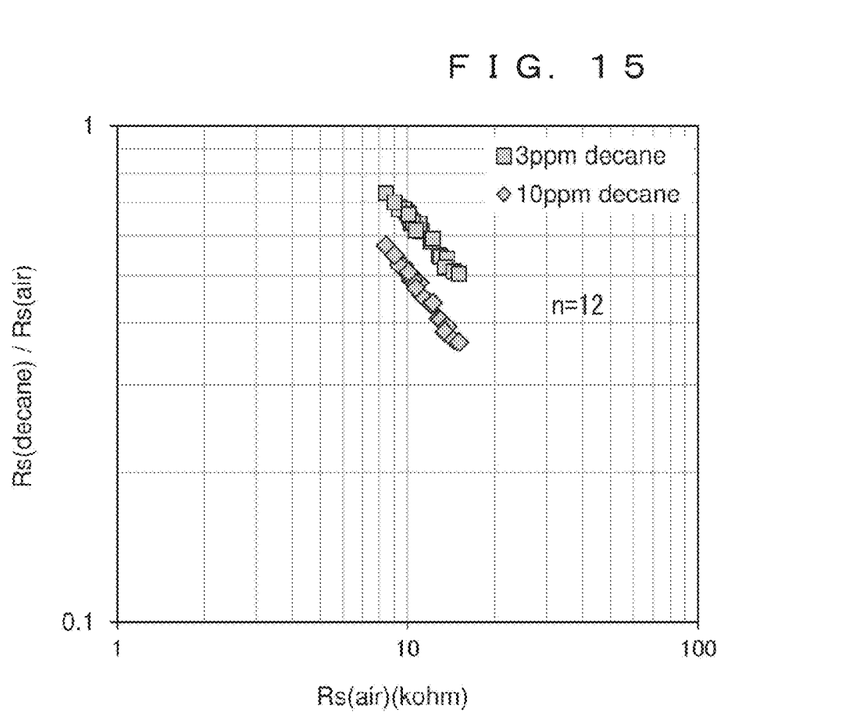
FIG. 15 A characteristic diagram indicating the correlation between the resistance in decane and the resistance in air (n=12).

As shown in FIGS. 6, 15, the ratio of gas sensor resistance between air and gas has a strong correlation to the resistance in air. In addition, the higher the resistance in air is, the larger the ratio of resistance between air and gas is. In the present specification, "air" is used as a word opposed to gas; air does not contain any gas that can be detected by the gas sensor and its humidity is arbitrary. According to the invention, the digital information processing device extracts the data representing the gas sensor resistance in air from the output of the gas sensor, for example, from the distribution of the output of the gas sensor. An output corresponding to the maximum resistance is, for example, extracted from the gas sensor output distribution for a predetermined period. Alternatively, within the gas sensor resistance distribution, a resistance located at a predetermined position may be extracted from the higher resistance side (for example, the top five % resistance or the top 10% resistance). These resistances correspond to gas sensor resistance in air. Since the higher the air resistance is, the larger the ratio of resistance between air and gas is; the extracted air resistance is used to generate the resistance that the gas sensor has in gas and is used as the comparison value for gas detection.

As a remark, the data representing the air resistance can be extracted without the gas sensor output distribution. For example, when detecting gas in exhaled air, the power supply of a detector is made on to heat the gas sensor, and the measurement is started when the gas sensor becomes possible to detect gas. In this case, the gas sensor resistance when the gas sensor has become possible to detect gas is usable as the air resistance. Further, when detecting smell from the discharge of a human by a gas sensor in a toilet seat, the gas sensor resistance when a person on the seat is detected is usable as the air resistance.

The comparison value for gas detection is the resistance that the gas sensor should have when a predetermined concentration of gas is present or may be another value corresponding to the resistance. In addition, when the gas sensor resistance is not more than the comparison value, a gas is assumed to be present, and the gas concentration is assumed not less than the predetermined concentration. Further, when the gas sensor resistance is larger than the comparison value, the gas concentration is assumed to be under the predetermined value. Furthermore, the gas sensor output may be the resistance, the electric conductivity that is the inverse of the resistance, or the voltage across the load resistor of the gas sensor. Instead of the ratio of the present air resistance and the initial air resistance, its inverse may be used. Further, instead of the ratio of the air resistance and the gas resistance, its inverse, namely the ratio of the gas resistance and the air resistance may be used. They are different to each other in the definition, the meaning of these data is the same. Here, the gas resistance means the resistance in gas, and the gas resistance means the resistance in gas.

Preferably, the digital information processing device stores data corresponding to the initial resistance of the gas sensor in air. Further, the digital information processing device stores at least a correction factor for generating the comparison value such that the larger a value corresponding to a ratio between the present air resistance of the gas sensor and the initial air resistance of the gas sensor is, the larger the ratio of the present air resistance and the resistance corresponding to the comparison value is. More preferably, the digital processing device stores data corresponding to the initial gas sensor resistance in gas Rgas0 and determines a correction factor C according to Rair/Rair0 to correct Rgas0 to a corrected comparison value for gas detection, such as C*Rgas 0. Alternatively, the digital information processing device may store at least a new correction factor D for converting Rair to the gas resistance Rgas according to a ratio of Rair/Rair0. In this case, the digital information processing device stores the data corresponding to the initial air resistance Rair0. For example, the correction factor D is multiplied by the air resistance Rair to a comparison value D*Rair for gas detection. The difference between C*Rga0 and D*Rair is whether Rgas0 is explicitly used or not. Regarding D*Rair, the correction factor D includes information about Rgas0/Rair.

Preferably, the digital information processing device stores initial resistances of the gas sensor in a gas at plural gas concentrations from a relatively lower gas concentration to a relatively higher gas concentration, stores a plurality of correction factors, from the relatively lower gas concentration to the relatively higher gas concentration, for generating a plurality of comparison values for gas detection such that a correction factor corresponding to the relatively lower gas concentration changes larger than a correction factor corresponding to the relatively higher gas concentration, in response to changes in the resistance of the gas sensor in air, and generates a plurality of comparison values for gas detection by multiplying the initial resistances of the gas sensor in gas by the correction factors at the same gas concentration.

Figure 7:
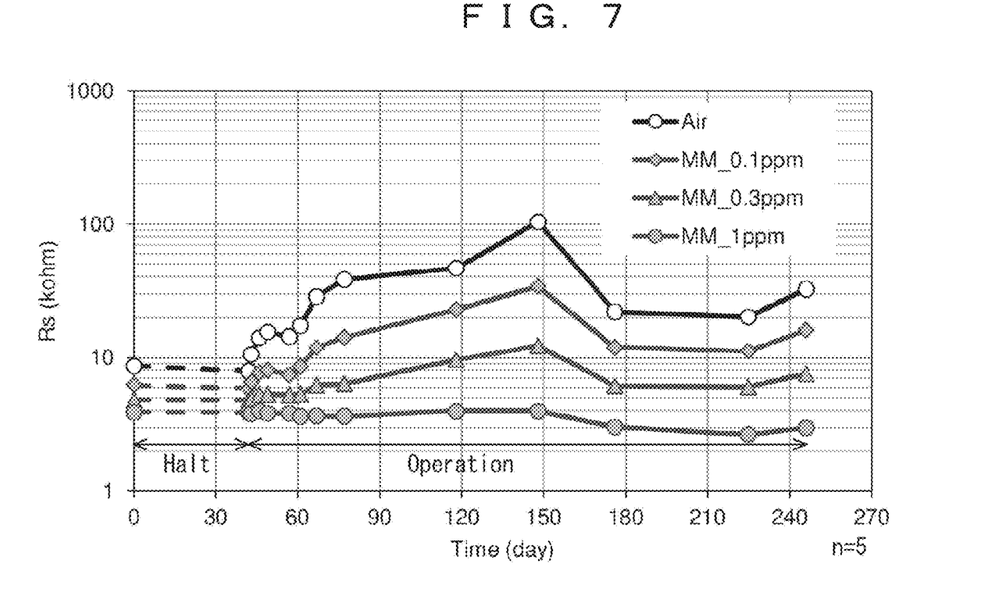
FIG. 7 A characteristic diagram indicating transitions of the resistances in methyl-mercaptan and air where the gas sensors were generally in operation (n=5).
Figure 8:
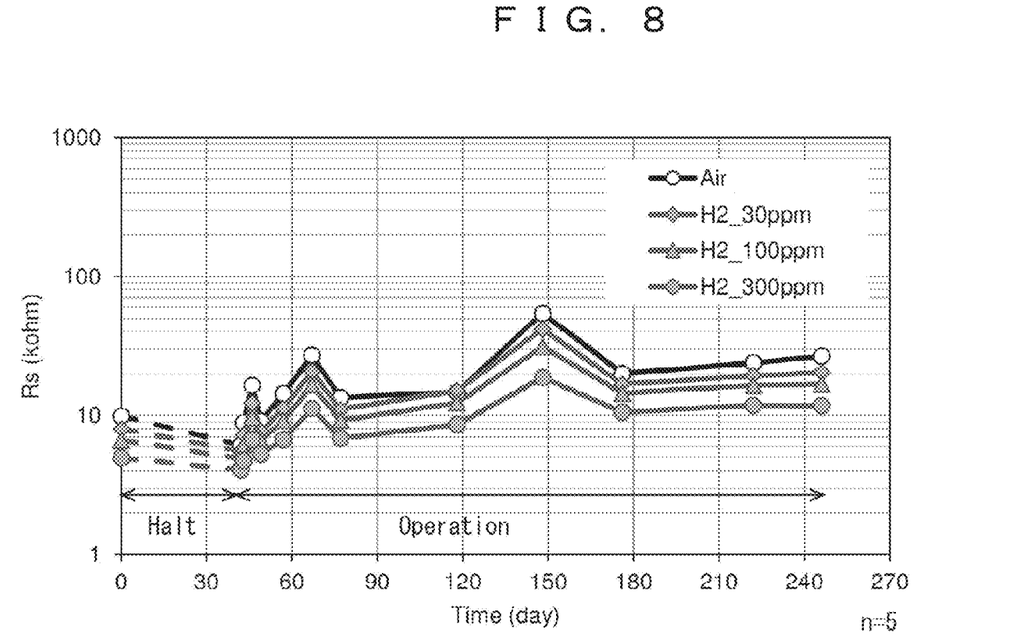
FIG. 8 A characteristic diagram indicating transitions of the resistances in hydrogen and air where the gas sensors were generally in operation (n=5).
Figure 9:
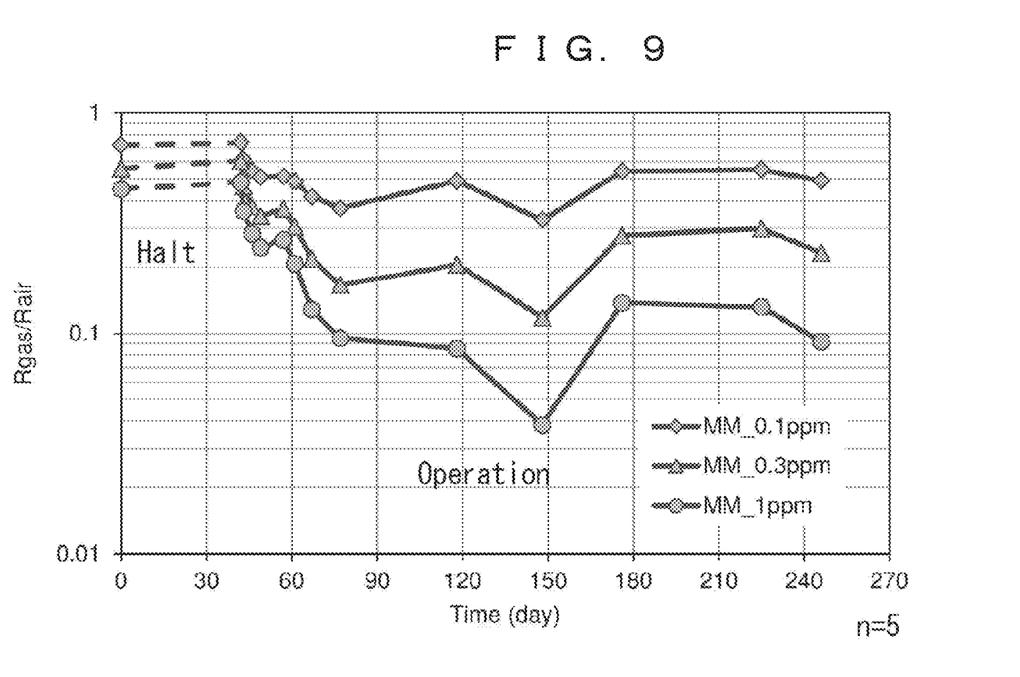
FIG. 9 A characteristic diagram indicating the ratios between the resistance in air and those in gas for the data in FIG. 7.
Figure 10:
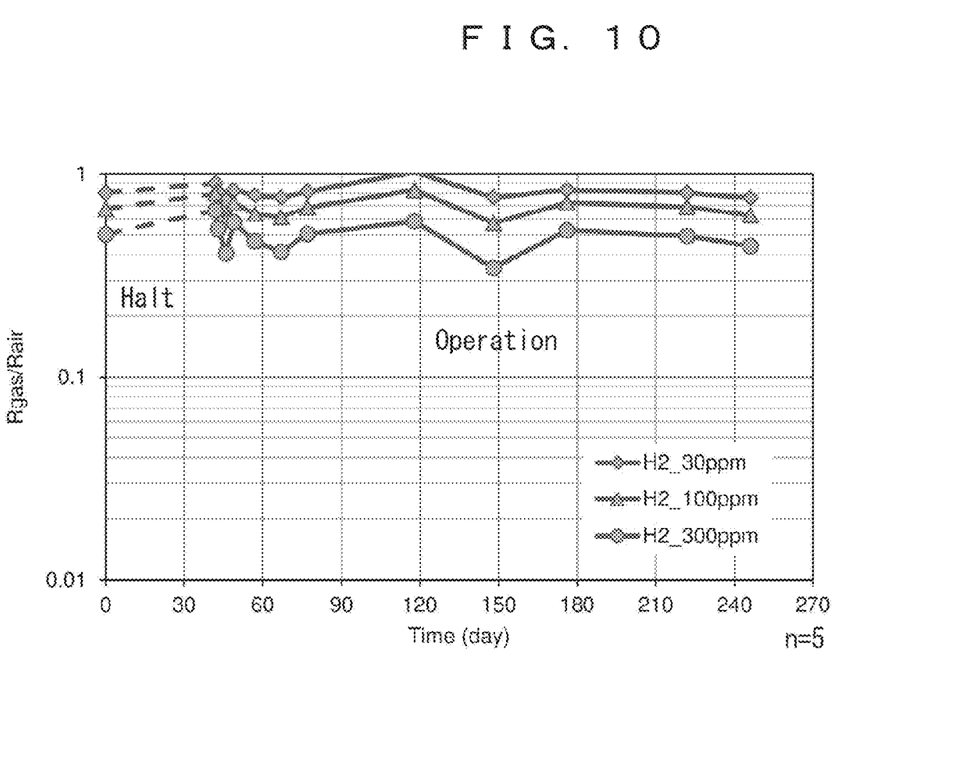
FIG. 10 A characteristic diagram indicating the ratios between the resistance in air and those in gas for the data in FIG. 8.
Figure 11:
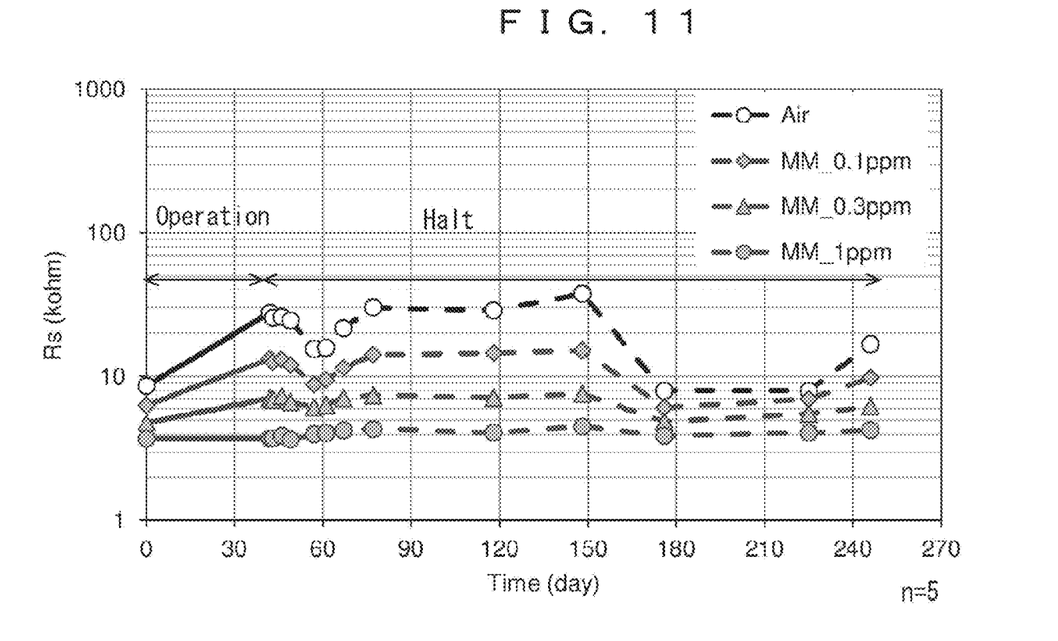
FIG. 11 A characteristic diagram indicating transitions of the resistances in methyl-mercaptan and air where the gas sensors were generally halted (n=5).
Figure 12:
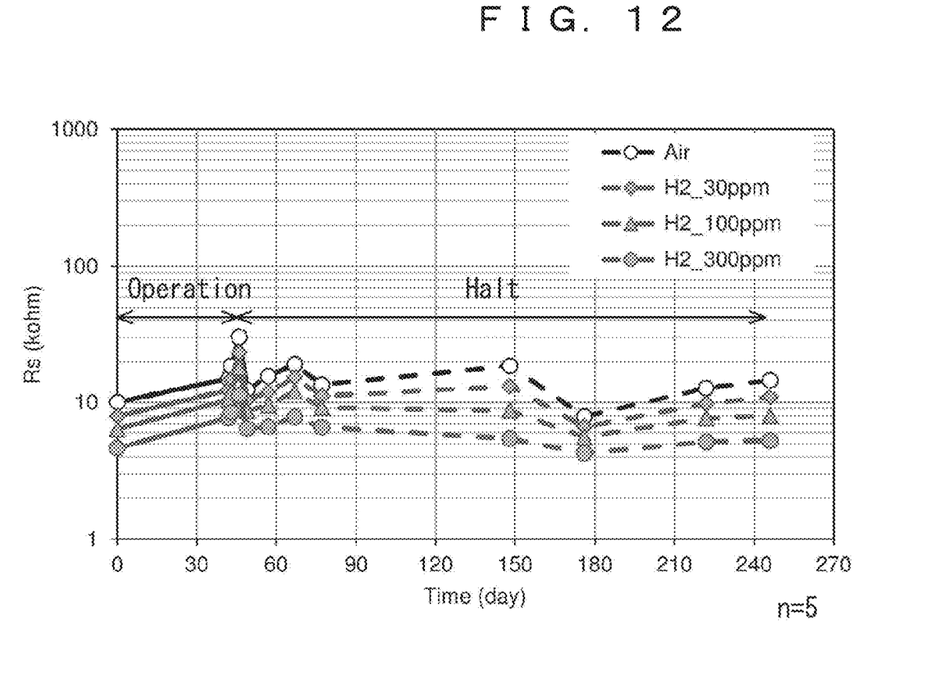
FIG. 12 A characteristic diagram indicating transitions of the resistances in hydrogen and air where the gas sensors were generally halted (n=5).
Figure 13:
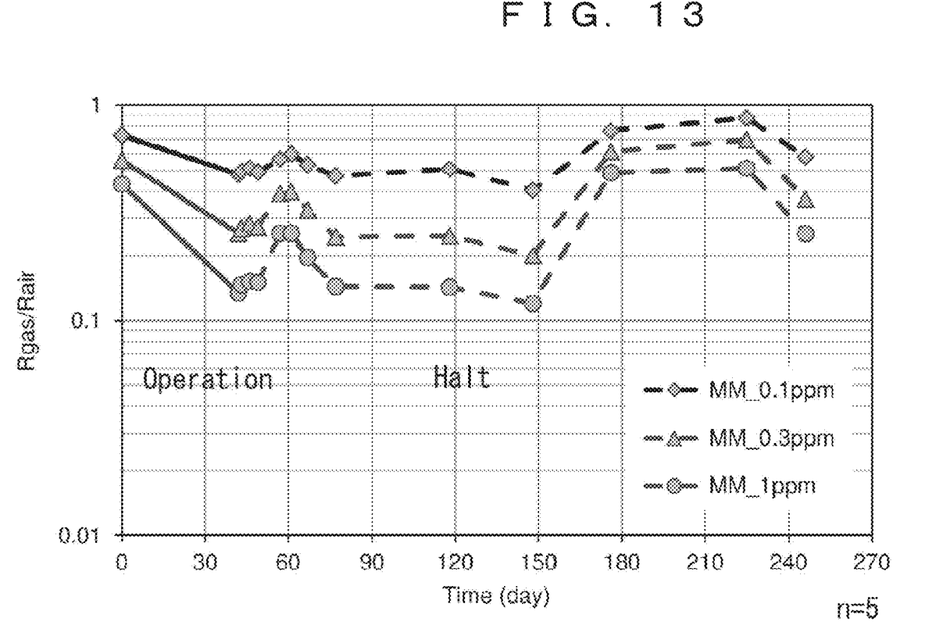
FIG. 13 A characteristic diagram indicating the ratios between the resistance in air and those in gas for the data in FIG. 11.
Figure 14:
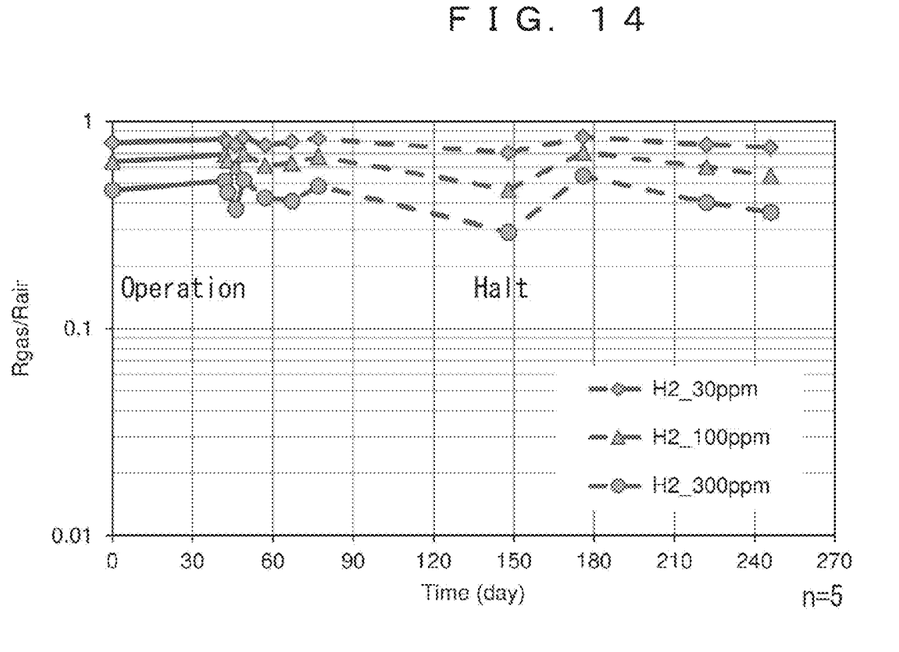
FIG. 14 A characteristic diagram indicating the ratios between the resistance in air and those in gas for the data in FIG. 12.

The above example will be described. As shown in the table in FIG. 5, the correction factors are provided for a range of the ratio Rair/Rair0 and also for a range of gas concentrations to the initial gas resistances. The correction factors change larger for the lower gas concentrations than for the higher gas concentrations when the gas sensor resistance in air changes. This well fits data in FIGS. 6 to 15. For example, data in FIGS. 7 and 8 reveal that accurate detection of gas concentration is enabled by the above measures.

Preferably, the digital information processing device generates a plurality of comparison values for gas detection by multiplying the extracted present air resistance of the gas sensor by a plurality of correction factors Di. The device stores the plurality of correction factors Di, from a relatively lower gas concentration to a relatively higher gas concentration and generates the plurality of comparison values such that a correction factor corresponding to the relatively higher gas concentration changes larger than a correction factor corresponding to the relatively lower gas concentration, when the extracted air resistance of the gas sensor changes.

Figure 5:
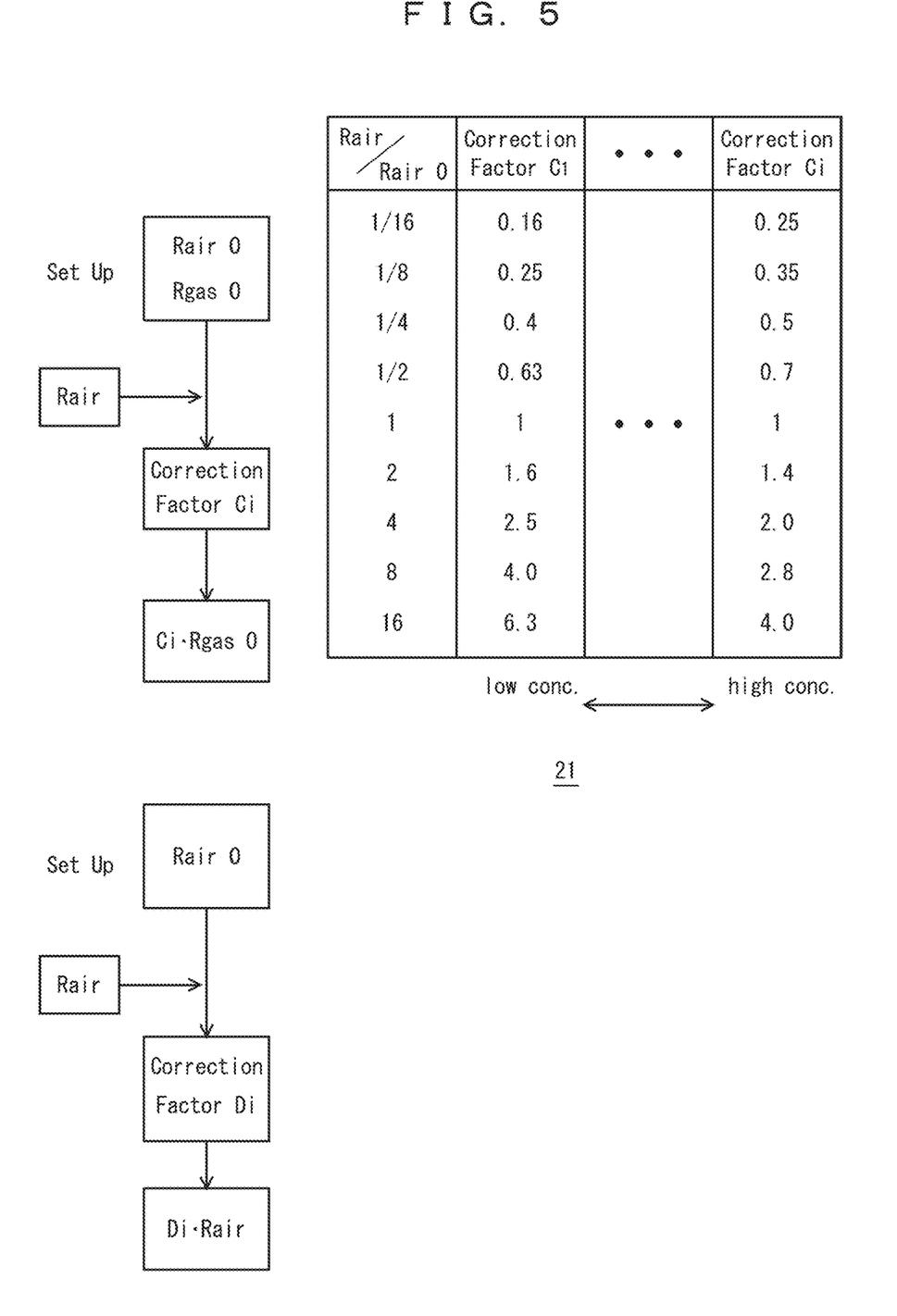
FIG. 5 A schematic view revealing the process with usage of a correction table.

The above example will be described. The correction factors Di convert the gas sensor resistance in air to resistance in gas. According to the gas sensor resistance in air, the correction factors Di are changed. Further, the correction factors for the high concentration range are changed larger than the correction factors for the low concentration range. This well fits data in FIGS. 6 to 15. For example, FIGS. 7 and 8 reveal that when the correction factors for conversion from air resistance to the gas resistance are made changed larger for the high concentration range than for the low concentration range, accurate detection of gas concentration is enabled. The correction factors are stored, for example as shown in FIG. 5, with indexes of ratios between air resistance and their initial values. By the way, the inverse of the above indexes, ratios between the initial air resistance and the measured air resistance, may be used.

Instead of the measured air resistance Rair, the initial air resistance Rair0 may be converted to the comparison values by the correction factors. In this case, the correction factors are inversely changed from the above example. Namely, the digital information processing device stores a plurality of correction factors, from the relatively lower gas concentration to the relatively higher gas concentration, such that the correction factor corresponding to the relatively lower gas concentration changes larger than the correction factor corresponding to the relatively higher gas concentration, when the air resistance of the gas sensor changes.

FEATURES FOR CARRYING OUT THE INVENTION

The best embodiment for carrying out the invention will be described.

EMBODIMENT

Figure 1:
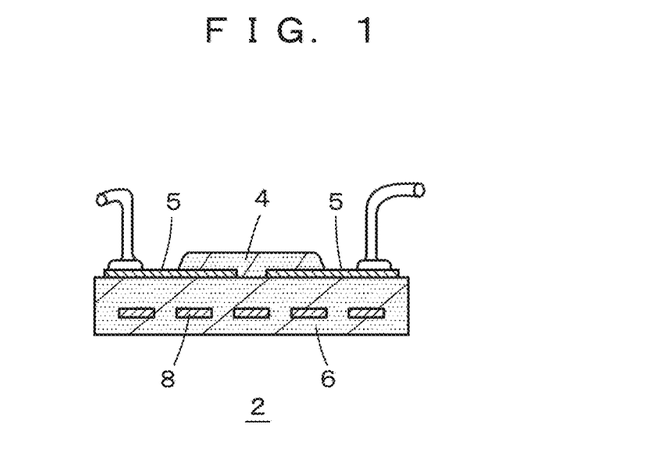
FIG. 1 A sectional view of a gas sensor used in the embodiment.

FIGS. 1 to 15 indicate the embodiment. FIG. 1 indicates the structure of a gas sensor 2. The sensor has a film of a metal oxide semiconductor 4 such as a $SnO_2$ film, a $WO_3$ film, an $In_2O_3$ film. These metal oxide semiconductors have a resistance that decreases in contact with reducing gases. The resistance decreases also when the ambient temperature increases and when the absolute humidity increases. The resistance of the metal oxide semiconductor 4 further changes according to trace quantities of gases included in air.

A pair of electrodes 5, 5, for example, are connected to the metal oxide semiconductor 4 for detecting its resistance, and a substrate 6 is provided with a heater 8 for heating the metal oxide semiconductor 4 to an operating temperature. The materials and structure of the gas sensor 2 are arbitrary. For example, the substrate 6 may be a thin film of $SiO_2/SiN_x/SiO_2$ or a thin film of $TaN_x$ that is provided over a cavity on a Si chip. Without the electrodes 5, 5, the heater 8 may be made in contact with the metal oxide semiconductor 4. When the resistance of the metal oxide semiconductor 4 changes, then, the synthetic resistance of the heater 8 and the metal oxide semiconductor 4 changes, and the synthetic resistance (the apparent resistance) is monitored.

Figure 2:
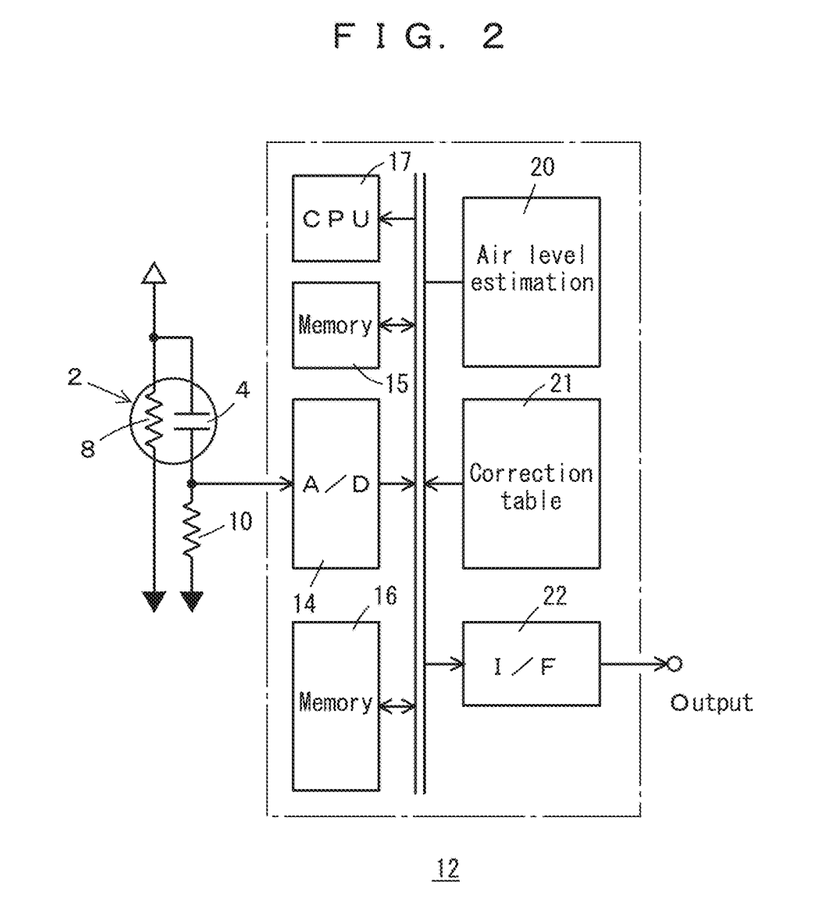
FIG. 2 A block diagram of a gas detector according to the embodiment.

FIG. 2 indicates the structure of a gas detector. The gas sensor 2 is supplied with electric power from a power source not shown, and an AD converter 14 in a micro-computer 12 converts the voltage across a load resistor 10 connected to the metal oxide semiconductor 4 to a digital value. A memory 15 stores the operation program of the micro-computer 12 and a memory 16 stores various data. A CPU 17 performs arithmetic operations and logical operations. An air level estimation means 20 extracts the air resistance of the metal oxide semiconductor 4 (the air resistance of the gas sensor 2). For the estimation of the air level (the resistance in air), the CPU 17 and the memories 15, 16 are used. A correction table 21 stores at least a correction factor for transforming the air resistance to a comparison value for gas detection, and the relevant data may be stored in a table format or another format. An output interface 22 outputs the detection result about gases.

The output of the gas sensor 2 may be treated as the resistance of the metal oxide semiconductor 4, the electric conductivity of the metal oxide semiconductor 4, or the voltage across the load resistor 10. In the following description, the voltage across the load resistor 10 is converted to the resistance of the metal oxide semiconductor 4 and the resistance is processed.

Figure 3:
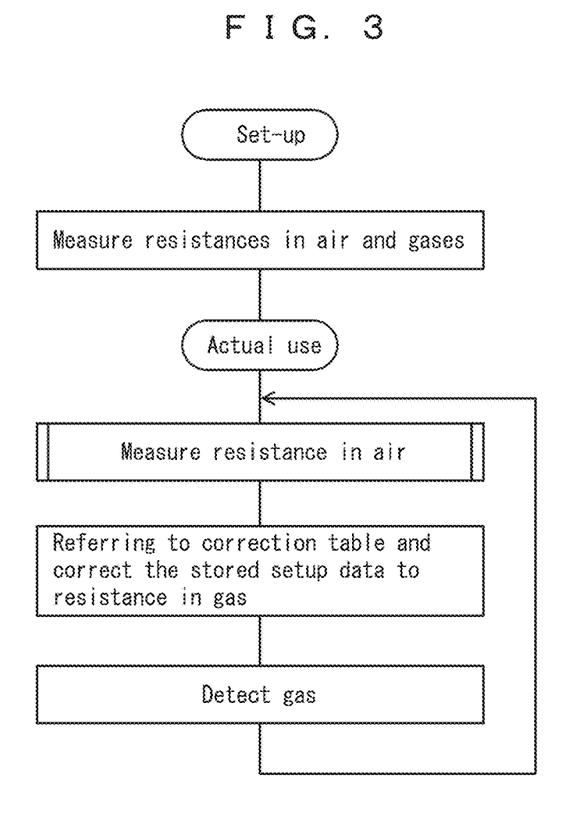
FIG. 3 A flowchart describing a gas detection algorithm according to the embodiment.
Figure 4:
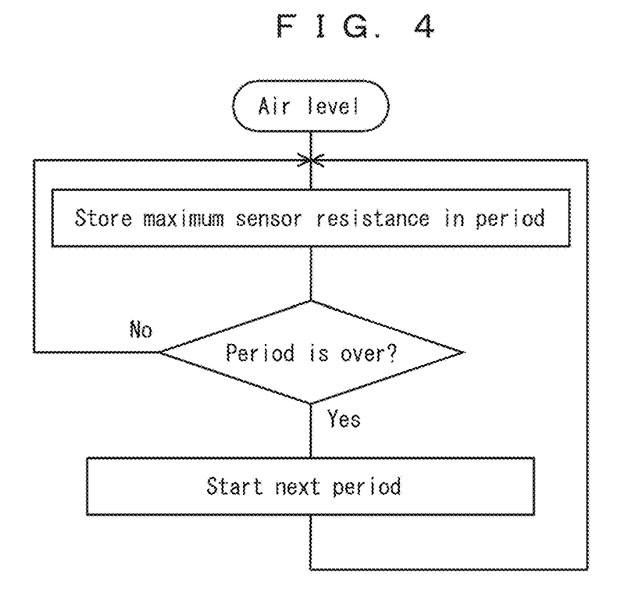
FIG. 4 A flowchart for estimating resistance in air according to the embodiment.

FIGS. 3 to 5 indicate the algorithm according to the embodiment. Before shipping the gas detector from a factory, the air resistance $Rair0$ and gas resistances at one or plural gas concentrations $Rgas0$ are measured and stored in the non-volatile memory 16. The air resistance $Rair$ of the gas sensor 4 is extracted according to the algorithm in FIG. 4 or the like. The maximum resistance of the gas sensor during a predetermined period is sampled. The period is, for example, not shorter than 10 minutes and not longer than one day. The sampled resistance is used as the air resistance during the next period. The period is preferably not shorter than 20 minutes and not longer than 4 hours.

Instead of extracting the maximum resistance, the histogram of the distribution of the resistance may be used such that the resistance, for example, at the top 5% position from the maximum is extracted from the histogram as the air resistance. Alternatively, a parameter representing the air resistance is generated and is modified such that, if a measured resistance is higher than the parameter, then, the parameter is increased by, for example, 10% and if the measured resistance is lower than the parameter, then, the parameter is decreased by, for example, 1%. In this case, similarly as the extraction of the high resistance portion in the histogram, the air resistance is extracted. In summary, the air resistance $Rair$ is within the high resistance portion in the past distribution of gas sensor resistance.

When the air resistance $Rair$ is extracted according to the algorithm in FIG. 4, then, $Rair/Rair0$ is calculated. A correction factor $C$ is retrieved from the correction table 21 according to $Rair/Rair0$. When initial resistances $Rgas0$ at plural gas concentrations are stored, plural correction factors $Ci$ at respective gas concentrations are stored in the table 21. $C*Rgas0$ or $Ci*Rgas0i$ are used as the comparison values for gas detection. Here, $Ci$ is a correction factor for an i-th gas concentration, and $Rgas0i$ is the initial resistance for the i-th gas concentration. This algorithm is indicated in the left-upper portion in FIG. 5. In addition, the format for storing the correction factors is arbitrary and is not limited to the table format. Further, between rows and columns in the table 21, linear interpolation is used to calculate the correction factor $C$, $Ci$.

When $Rair/Rair0$ is larger than 1, the correction factors $C$, $Ci$ are larger than 1 and smaller than $Rair/Rair0$. When $Rair/Rair0$ is smaller than 1, the correction factors $C$, $Ci$ are smaller than 1 and larger than $Rair/Rair0$. The retrieved correction factors $C$, $Ci$ are, for example, multiplied by the stored initial gas resistance $Rgas0$ for generating the comparison values for gas detection $C*Rgas0$ or $Ci*Rgas0$. When the actual gas sensor resistance is smaller than or equal to a generated comparison value, then, the gas detector detects a gas having a predetermined concentration or more. Namely, gas is detected based upon the comparison with $C*Rgas0$ or $Ci*Rgas0i$ and the gas sensor resistance.

When $C*Rgas0$ is set as $Rgas$, the correction factor $C$ is smaller than $Rair/Rair0$, when $Rair/Rair0$ is larger than 1. Therefore, $Rgas=C*Rgas0<Rair/Rair0*Rgas0$. This formula leads to $Rgas/Rair<Rgas0/Rair0$, namely $Rair/Rgas>Rair0/Rgas0$. This means that when the air resistance is large ($Rah>Rair0$), then, the ratio between the resistances in air and gas is large.

Instead of the correction of $Rgas0$ by the correction factor $C$, another correction factor $D$ may be generated according to $Rair/Rair0$ and $D*Rair$ may be used as a comparison value for gas detection, as shown in the left-lower portion in FIG. 5. In this case, $D$ is smaller than 1. For example, when gas is detected at plural concentrations, the larger the gas concentration is, the smaller $D$ is. A number i is counted from the lowest gas concentration to the highest gas concentration, the plural correction factors $Di$ are stored in the table 21, and the correction factors $Di$ become smaller when the number i increases. $Di$ indicates the resistance ratio between the resistances in gas and air, $Di$ becomes smaller when $Rair/Rair0$ is larger (when the air resistance is large), and becomes larger when $Rair/Rair0$ is smaller (when the air resistance is small) In this case, $Rair0$ is stored, but $Rga0$ is not needed to be stored. In addition, when $Rair/Rsair0=1$, (when the air resistance is not changed from its initial value), $Di*Rair$ is equal to the initial gas sensor resistance $Rgas0i$ at the i-th gas concentration. Namely, $Di*Rair=Di*Rair0=Rgas0i$ ($Rair=Rair0$).

FIGS. 6 to 14 reveal the behavior of gas sensor resistance in air, 0.1 to 1 ppm methyl-mercaptan (MM), and 30 to 300 ppm hydrogen. The number of the sensors was five and the averages of the five sensors are indicated. The background air was air-conditioned laboratory air.

FIGS. 6 to 14 Indicate when the air resistance is high, then, the gas resistance is also high (FIGS. 7, 8, 11, and 12), and when the air resistance is high, then, the ratio between air resistance and gas resistance becomes larger (FIGS. 9, 10, 13, and 14). Thus, the larger Rair/Rair0 is, the larger the ratio between the air resistance and the gas resistance Rir/Rgas is. Therefore, the correction factor C is determined and stored such that the above condition is satisfied, and C multiplied by Rgas0 is used as the comparative value for gas detection. Alternatively, the correction factor D is stored such that the above condition is satisfied, and D*Rair is used for gas detection. They enable the detection of low concentration gases.

FIG. 15 reveals the correlation of the ratios of the resistances in decane (3 ppm and 10 ppm) and air, and the resistances in air. The number of sensors was 12 and their average is shown. The temperature was 20 degree Celsius, and the relative humidity was adjusted to 65%. When the decane concentration was fixed, the higher the air resistance was, the smaller the ratio of the resistance in decane and resistance in air was. The correlation was very strong. Therefore, also in this case, the correction factor C is transformed to the comparison value C*Rgas0 for gas detection. Alternatively, the correction factor D is transformed to the comparison value D*Rair for gas detection.

SYMBOL LIST 2 gas sensor
4 metal oxide semiconductor
5 electrodes
6 substrate
8 heater
10 load resistor
12 micro-computer
14 AD converter
15, 16 memory
17 CPU
20 air level estimation means
21 correction table
22 output interface

What is claimed is:

1. A gas detector comprising:
a metal oxide semiconductor gas sensor having resistance decreasing in reducing gases; and
a digital information processing device treating output of the gas sensor and comparing the output with a comparison value for gas detection in order to detect gas; wherein
the digital information processing device is configured and programmed to:
extract data representing resistance of the gas sensor in air from the output of the gas sensor;
generate the comparison value such that the larger the resistance of the gas sensor in air is, the larger a ratio between the resistance of the gas sensor in air and a resistance value corresponding to the comparison value is;
store data corresponding to initial resistance of the gas sensor in air; and
store a correction factor for generating the comparison value such that the larger a value corresponding to a ratio between the resistance of the gas sensor in air and the initial resistance of the gas sensor in air is, the larger the ratio is; and
the digital information processing device is further configured and programmed to:
store initial resistances of the gas sensor in a gas at plural gas concentrations from a relatively lower gas concentration to a relatively higher gas concentration;
store a plurality of correction factors, from the relatively lower gas concentration to the relatively higher gas concentration, for generating a plurality of comparison values for gas detection such that a correction factor corresponding to the relatively lower gas concentration changes larger than a correction factor corresponding to the relatively higher gas concentration, in response to changes in the resistance of the gas sensor in air; and
generate a plurality of comparison values for gas detection by multiplying the initial resistances of the gas sensor in gas by the correction factors at a same gas concentration.

2. A gas detector comprising:
a metal oxide semiconductor gas sensor having resistance decreasing in reducing gases; and
a digital information processing device treating output of the gas sensor and comparing the output with a comparison value for gas detection in order to detect gas; wherein
the digital information processing device is configured and programmed to:
extract data representing resistance of the gas sensor in air from the output of the gas sensor;
generate the comparison value such that the larger the resistance of the gas sensor in air is, the larger a ratio between the resistance of the gas sensor in air and a resistance value corresponding to the comparison value is;
store data corresponding to initial resistance of the gas sensor in air; and
store a correction factor for generating the comparison value such that the larger a value corresponding to a ratio between the resistance of the gas sensor in air and the initial resistance of the gas sensor in air is, the larger the ratio is; and
the digital information processing device is further configured and programmed to:
store a plurality of correction factors, from a relatively lower gas concentration to a relatively higher gas concentration, for generating comparison values for gas detection such that a correction factor corresponding to the relatively lower gas concentration changes larger than a correction factor corresponding to the relatively higher gas concentration, in response to changes in the resistance of the gas sensor in air; and
generate the comparison values by multiplying the initial resistances of the gas sensor in air by the plurality of correction factors.

3. A gas detection method using a metal oxide semiconductor gas sensor having resistance decreasing in reducing gases and a digital information processing device treating output of the gas sensor and comparing the output with a comparison value for gas detection in order to detect gas, the method comprising:
a step for extracting data representing resistance of the gas sensor in air from the output of the gas sensor;
a step for generating the comparison value such that the larger the resistance of the gas sensor in air is, the larger a ratio between the resistance of the gas sensor in air and a resistance value corresponding to the comparison value is;

a step for storing data corresponding to initial resistance of the gas sensor in air; and a step for storing a correction factor for generating the comparison value such that the larger a value corresponding to a ratio between the resistance of the gas sensor in air and the initial resistance of the gas sensor in air is, the larger the ratio is; wherein in the step for storing the correction factor, a plurality of correction factors, from a relatively lower gas concentration to a relatively higher gas concentration, are stored for generating comparison values for gas detection such that a correction factor corresponding to the relatively lower gas concentration changes larger than a correction factor corresponding to the relatively higher gas concentration, in response to changes in the resistance of the gas sensor in air; and in the step for generating the comparison value, the comparison values are generated by multiplying the initial resistances of the gas sensor in air by the plurality of correction factors.

\* \* \* \* \*